(12) United States Patent
Burkholder et al.

(10) Patent No.: US 7,897,600 B2
(45) Date of Patent: Mar. 1, 2011

(54) AMINO PYRAZOLE COMPOUND

(75) Inventors: Timothy Paul Burkholder, Carmel, IN (US); Joshua Ryan Clayton, Fishers, IN (US); Liandong Ma, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/632,879

(22) Filed: Dec. 8, 2009

(65) Prior Publication Data

US 2010/0152181 A1 Jun. 17, 2010

Related U.S. Application Data

(60) Provisional application No. 61/122,854, filed on Dec. 16, 2008.

(51) Int. Cl.
*A61K 31/5377* (2006.01)
*C07D 413/14* (2006.01)
(52) U.S. Cl. .................... 514/233.2; 544/117
(58) Field of Classification Search .............. 514/233.2; 544/117
See application file for complete search history.

(56) References Cited

U.S. PATENT DOCUMENTS

| 2007/0083044 A1 | 4/2007 | Paruch et al. |
| 2007/0191369 A1 | 8/2007 | Lauffer et al. |
| 2008/0085909 A1 | 4/2008 | Roughton et al. |

FOREIGN PATENT DOCUMENTS

| WO | WO02059112 | 8/2002 |
| WO | WO02066461 | 8/2002 |
| WO | WO02068415 | 9/2002 |
| WO | WO03055876 | 7/2003 |
| WO | WO2006087530 | 8/2006 |
| WO | WO2006087538 | 8/2006 |
| WO | WO 2007/009773 A1 | 1/2007 |
| WO | WO 2007/044426 A2 | 4/2007 |
| WO | WO2007064797 | 6/2007 |
| WO | WO2008030579 | 3/2008 |
| WO | WO2008143674 | 11/2008 |
| WO | WO2009062059 | 5/2009 |

*Primary Examiner*—Rebecca L Anderson
(74) *Attorney, Agent, or Firm*—Elizabeth A. McGraw

(57) ABSTRACT

The present invention provides amino pyrazole compounds useful in the treatment of chronic myeloproliferative disorders and various cancers, e.g., glioblastoma, breast cancer, multiple myeloma, prostate cancer, and leukemias.

9 Claims, No Drawings

AMINO PYRAZOLE COMPOUND

Janus kinase 2 (JAK2) is a member of the tyrosine kinase family which is involved in cytokine signaling. JAK2 has a pivotal role in the erythropoietin (EPO) signaling pathway, including erythrocyte differentiation and Stat5 activation. Recent studies have demonstrated that patients with chronic myeloproliferative disorders such as polycythemia vera, essential thrombocytosis, and myelosclerosis with myeloid metaplasia and thrombotic disorders such as activated protein C resistance, splanchnic vein thrombosis, Budd-Chiari Syndrome, and portal vein thrombosis frequently have acquired activating mutations in JAK2. The mutation, a valine-to-phenylalanine substitution at amino acid position 617, leads to constitutive tyrosine phosphorylation activity, by an unknown mechanism. The constitutive activity of mutant JAK2 leads to increased levels of phosphorylated JAK2, pSTAT5, and STAT5 transcriptional activity, which leads to the pathogenesis of myeloproliferative disorders and leukemias, such as atypical chronic myeloid leukemia. In addition, JAK2 is activated by interleukin-6-dependent autocrine loop or other genetic alterations in solid and hematologic tumors, e.g., glioblastoma, breast cancer, multiple myeloma, prostate cancer, primary and secondary acute myeloid leukemia, T-lineage and B-lineage acute lymphoblastic leukemia, myelodysplasia syndrome.

Various amino pyrazole tyrosine kinase inhibitors have been reported. See for example, WO06087538 and WO2007064797.

However, there is still a need for further compounds that inhibit tyrosine kinases such as JAK2. The present invention provides a novel amino pyrazole compound believed to have clinical use for treatment of myeloproliferative disorders in which the JAK2 signaling pathway is activated or in which JAK/STAT signaling is dysregulated.

The present invention provides 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof.

The present invention provides a method of treating chronic myeloproliferative disorders selected from the group consisting of polycythemia vera, essential thrombocytosis, and myelosclerosis with myeloid metaplasia in a mammal comprising administering to a mammal in need of such treatment an effective amount of 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof.

The present invention also provides a method of treating glioblastoma, breast cancer, multiple myeloma, prostate cancer, and leukemias, such as atypical chronic myeloid leukemia, primary and secondary acute myeloid leukemia, T-lineage and B-lineage acute lymphoblastic leukemia, myelodysplasia syndrome, and myeloproliferative disorders in a patient comprising administering to a patient in need of such treatment an effective amount of 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof.

The present invention also provides a pharmaceutical composition comprising 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof, and a pharmaceutically acceptable carrier, diluent or excipient.

This invention also provides 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof, and a pharmaceutically acceptable carrier, diluent or excipient in combination with another therapeutic ingredient.

This invention also provides 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof for use as a medicament. Additionally, this invention provides use of 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof in the manufacture of a medicament for treating chronic myeloproliferative disorders. In particular these chronic myeloproliferative disorders are selected from the group consisting of polycythemia vera, essential thrombocytosis, and myelosclerosis with myeloid metaplasia. Furthermore, this invention provides a pharmaceutical composition for treating chronic myeloproliferative disorders selected from the group consisting of polycythemia vera, essential thrombocytosis, and myelosclerosis with myeloid metaplasia comprising 3-(4-chloro-2-fluorobenzyl)-2-methyl-N-(5-methyl-1H-pyrazol-3-yl)-8-(morpholinomethyl)imidazo[1,2-b]pyridazin-6-amine or a pharmaceutically acceptable salt thereof as an active ingredient.

It will be understood by the skilled reader that the compound of the present invention is capable of forming salts. The compound of the present invention is an amine, and accordingly reacts with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499; S. M. Berge, et al., "Pharmaceutical Salts," *Journal of Pharmaceutical Sciences*, Vol 66, No. 1, January 1977.

The following preparations and examples are named using ChemDraw Ultra, Version 10.0.

SCHEME 1

Preparation 1

1-(4-Methoxybenzyl)-5-methyl-1H-pyrazol-3-amine

Method 1

In a 1 L round bottom flask, combine 5-amino-3-methylpyrazole (22.8 g, 234.8 mmol) and N-methylpyrrolidone (200 mL). Cool flask to 0° C. and place under nitrogen. Add sodium hydroxide (9.39 g, 1.0 equivalent (equiv.)) to the flask and stir for 30 minutes (min) Add a solution of alpha-chloro-4-methoxytoluene (31 mL, 1.0 equiv.) in N-methylpyrrolidone (100 mL) to the flask drop-wise. Let the reaction warm to room temperature (RT) slowly overnight. Dilute the reaction with water, and extract with ethyl acetate (EA). Wash the organics with aqueous saturated sodium chloride. Concentrate in vacuo. Purify on a plug of silica (hexane→2:1 hexane:EA→3:2 hexane:EA→1:1 hexane:EA→1:2 hexane:

EA→EA). Concentrate the desired fractions to give the title compound (10.8 g, 21%). LCMS (4 min)=218.0 (M+1).

Method 2

A. (E)-tert-Butyl 2-(4-methoxybenzylidene)hydrazinecarboxylate

Add 4-methoxybenzaldehyde (400 g, 2.94 mol) over 20 min to a solution of tert-butyl carbazate (400 g, 2.94 mol) in toluene (750 mL) at 50° C. Heat to reflux over a period of 1 hour (h), collecting water in an azeotrope with the toluene. After no further water is collected, cool to 60° C. Add hexanes until the product precipitates from solution. Cool the bath further to 20° C. Collect the solids by filtration and dry using a nitrogen press to afford the title compound (750.5 g, 91%). $^1$H NMR [400 MHz, dimethyl sulfoxide-$d_6$ (DMSO-$d_6$)] δ 10.6-10.8 (bs, 1H), 7.88-8.0 (S, 1H), 7.5-7.55 (d, 2H), 6.95-7.0 (d, 2H), 1.45 (s, 9H). ES/MS (m/z): 249 [M-H].

B. tert-Butyl 2-(4-methoxybenzyl)hydrazinecarboxylate

Add 10% palladium on carbon (water wet, 20 g) slurried in EA (100 mL) to a sealed pressure reactor via vacuum transfer. Rinse transfer line with a minimal amount of EA. Charge (E)-tert-butyl 2-(4-methoxybenzylidene)hydrazinecarboxylate (320 g, 1.28 mol) dissolved in tetrahydrofuran (THF, 1000 mL) via vacuum transfer and rinse line with a minimal amount of THF. Pressurize the reactor to 50 PSI with $H_2$ and mix the contents of the reactor at 20±10° C. Continue the reaction, maintaining the hydrogen pressure at 50 PSI, until no further hydrogen uptake is observed. Filter the reaction solution to remove the catalyst and wash the catalyst filter-cake with THF (500 mL). Add the wash to the reaction filtrate. Concentrate the solution in vacuo to obtain the title compound (337 g, 86%) as an oil. $^1$H NMR (400 MHz, DMSO-$d_6$) δ 8.1-8.3 (s, 1H), 7.1-7.3 (d, 2H), 6.8-6.9 (d, 2H), 4.4-4.6 (bs, 1H), 3.7-3.8 (s, 2H), 3.6-3.7 (s, 3H), 1.3-1.5 (s, 9H).

C. (4-Methoxybenzyl)hydrazine dihydrochloride

To a solution of 4 N hydrogen chloride in dioxane (2000 mL, 8.00 mol HCl), add tert-butyl 2-(4-methoxybenzyl)hydrazinecarboxylate (324 g, 1.09 mol) dissolved in a minimal amount of dioxane, slowly over a period of 1 h. A precipitate gradually forms. Allow the solution to stir 16 h at 20±5° C. Collect the solids by filtration. Slurry the solids in heptane (2000 mL) and isolate the solids by filtration. Dry the solids using a nitrogen press to give the title compound (242.3 g, 1.08 mol, 98%). $^1$H NMR (400 MHz, DMSO-$d_6$) δ 8.2-9.0 (bs, 5H), 7.3-7.4 (d, 2H), 6.8-7.0 (d, 2H), 4.0 (s, 2H), 3.7 (s, 3H).

D. 1-(4-Methoxybenzyl)-5-methyl-1H-pyrazol-3-amine and 1-(4-methoxybenzyl)-3-methyl-1H-pyrazol-5-amine Combine potassium tert-butoxide (191.89 g, 1.71 mol) and THF (2000 mL) at 22° C. Mix until a homogeneous solution is obtained. Cool to 5° C. Add a premixed solution of acetonitrile (84.25 g, 2.05 mol) and methyl acetate (126.7 g, 1.71 mol) to the potassium tert-butoxide solution over 45 min maintaining a temperature less than 10° C. After the addition is complete, allow the reaction to warm to 20±5° C. and stir for about 2 h. Add (4-methoxybenzyl)hydrazine dihydrochloride (250 g) portion-wise to the reaction over about 5 min, followed by 4 N hydrogen chloride in dioxane (262.5 g, 1.00 mol) at a rate that maintains the temperature <30° C. When the addition is complete, allow to stir at 25±5° C. for about 16 h. Isolate the solids by filtration and wash with THF (500 mL). Slurry the crude solids in dichloromethane (DCM, 4 L) and water (2 L) adjusting the pH to >10 with 5 N NaOH. Allow the layers to settle and collect the organic phase. Wash the aqueous phase with DCM (2 L). Combine the organic phases and dry over anhydrous sodium sulfate and concentrate the solution to a solid in vacuo to afford 165 g of the crude. Heat the crude in isopropyl acetate (660 mL) to reflux to dissolve as many solids as possible. Cool to 33° C. and add hexane (600 mL) slowly over 1 h. Cool to 10° C. and maintain the temperature at 10° C. for 10 min. Isolate the solids by filtration, wash with hexane (200 mL), and dry using a nitrogen press to afford a mixture of the title compounds (91.5 g, 0.4 mol, 47%). $^1$H NMR (400 MHz, DMSO-$d_6$) δ 7.2-7.3 (d, 2H), 6.7-6.9 (d, 2H), 5.1 (bs, 2H), 5.0 (s, 1H), 4.9 (s, 2H), 3.6-3.8 (s, 3H), 1.9 (s, 3H).

Note: these intermediates can be separated by chromatography; however in this case, they are isolated as a mixture and can be used in the final sequence below which involves removal of the benzyl protection group resulting in the same product.

Preparation 2

2-Chloro-1-(4-chloro-2-fluorophenyl)ethanone

In a 1 L round bottom flask combine 4'-chloro-2'-fluoroacetophenone (40 g, 231.8 mmol), heptane (120 mL), and methanol (16 mL). Cool to 0° C. and place under nitrogen. Dissolve sulfuryl chloride (21.5 mL, 1.15 equiv.) in heptane (120 mL) and charge to an addition funnel Add drop-wise to the reaction over 60 min. Stir for 2.5 h at 0° C.; a white precipitate forms during this time. Charge the addition funnel with 1 M sodium bicarbonate (400 mL) then add to the reaction drop-wise. After all gas evolution stops, filter the biphasic suspension to collect the title compound (38.18 g, 80%) as white needles. $^1$H NMR (DMSO-$d_6$) δ 5.00 (d, 2H, J=2.5 Hz), 7.43 (m, 1H), 7.63 (m, 1H), 7.89 (t, 1H, J=8.4 Hz).

Preparation 3

(E)-N'-(6-Chloropyridazin-3-yl)-N,N-dimethylacetimidamide

In a 2 L round bottom flask combine 3-chloro-6-pyridazinamine (43.2 g, 333.5 mmol), toluene (500 mL), and N,N-dimethylacetamide dimethyl acetal (67.8 mL, 1.25 equiv.). Attach a reflux condenser then heat to reflux for 2 h. Let cool to RT. Concentrate in vacuo. Triturate the crude material with hexanes and filter to isolate the title compound (60.4 g, 91%) as a light tan solid. MS=199.0 (M+1).

Preparation 4

(4-Chloro-2-fluorophenyl)(6-chloro-2-methylimidazo[1,2-b]pyridazin-3-yl)methanone In a round bottom flask combine (E)-N'-(6-chloropyridazin-3-yl)-N,N-dimethylacetimidamide (36.61 g, 184.3 mmol), 2-chloro-1-(4-chloro-2-fluorophenyl)ethanone (38.15 g, 1 equiv.), and dimethylformamide (150 mL). Place under nitrogen then heat at 120° C. for 4 h. Let cool to RT and stir overnight. Dilute with EA (1 L) and water (500 mL).

Extract organics three times with water followed by aqueous saturated sodium chloride aqueous. Dry organics over anhydrous magnesium sulfate. Filter and concentrate in vacuo. Purify by silica plug (hexane→4:1 hexane:EA→3:1 hexane: EA→2:1 hexane:EA→1:1 hexane:EA) and isolate the title compound (33.8 g, 57%) as a light green solid. LCMS (4 min=324.0, 326.0, M+1).

Preparation 5

2-((6-Chloro-3-(4-chloro-2-fluorobenzoyl)-2-methylimidazo[1,2-b]pyridazin-8-yl)methyl)isoindoline-1,3-dione Combine (4-chloro-2-fluorophenyl)(6-chloro-2-methylimidazo[1,2-b]pyridazin-3-yl)methanone (5.6 g, 17.3 mmol), N-phthaloylglycine (6.0 g, 1.7 equiv.), acetonitrile (60 mL), water (15 mL), trifluoroacetic acid (0.26 mL, 0.2 equiv.), and silver nitrate (294 mg, 0.1 equiv.) in a round bottom flask with attached addition funnel and place under nitrogen. Heat to 70° C. and maintain at this temperature for 15 min. Dissolve ammonium persulfate (7.1 g, 1.8 equiv.) in water (15 mL) and charge to an addition funnel Add dropwise to the reaction flask over approximately 20 min. Heat reaction at 70° C. for 1 h. A precipitate forms during this time; filter via Buchner funnel to isolate the title compound crude (7.3 g, 87%) as an off-white solid. LCMS (4 min)=483.0, 485.0, M+1).

Preparation 6

(8-(Aminomethyl)-6-chloro-2-methylimidazo[1,2-b]pyridazin-3-yl)(4-chloro-2-fluorophenyl)methanone Combine 2-((6-chloro-3-(4-chloro-2-fluorobenzoyl)-2-methylimidazo[1,2-b]pyridazin-8-yl)methyl)isoindoline-1,3-dione (7.30 g, 15.1 mmol), ethanol (200 mL), and hydrazine (1.45 mL, 3 equiv.) in a round bottom flask and place under nitrogen. Stir for 2 days at RT. Heat for 2 h at 50° C. then concentrate the reaction in vacuo. Dilute with EA. Wash the organics with 1 N HCl (aq) to pull product into the aqueous layer. Make the aqueous layer basic with 1 N NaOH (aq) and extract with EA. Wash the EA layer with aqueous saturated sodium chloride, and dry over anhydrous magnesium sulfate. Filter and concentrate in vacuo to give the title compound crude (1.2 g, 23%) as a light green solid. MS=355.0, 353.0 (M+1).

Preparation 7

(4-Chloro-2-fluorophenyl)(6-chloro-2-methyl-8-(morpholinomethyl)imidazo[1,2-b]pyridazin-3-yl)methanone Combine (8-(aminomethyl)-6-chloro-2-methylimidazo[1,2-b]pyridazin-3-yl)(4-chloro-2-fluorophenyl)methanone (1.15 g, 3.3 mmol), water (12 mL), potassium carbonate (495 mg, 1.1 equiv.), and 2-bromoethyl ether (0.47 mL, 1.1 equiv) in a 20 mL microwave reaction vessel. Seal with a crimp cap then heat in a microwave reactor at 120° C. for 20 min. Cool to RT and partition between EA and water. Wash EA layer with aqueous saturated sodium chloride, and dry over anhydrous magnesium sulfate. Filter and concentrate in vacuo. Purify on silica gel (4:1 hexane:EA→2:1 hexane:EA→1:1 hexane:EA) to give the title compound (0.43 g, 31%) as a light yellow foam. LCMS (4 min)=423.0, 425.0, M+1.

Preparation 8

(4-Chloro-2-fluorophenyl)(6-chloro-2-methyl-8-(morpholinomethyl)imidazo[1,2-b]pyridazin-3-yl)methanol Combine (4-chloro-2-fluorophenyl)(6-chloro-2-methyl-8-(morpholinomethyl)imidazo[1,2-b]pyridazin-3-yl)methanone (0.43 g, 1.0 mmol) and methanol (15 mL) in a round bottom flask. Place under nitrogen and cool to 0° C. Add sodium borohydride (58 mg, 1.5 equiv.) in one portion. Stir for 5 min at this temperature then remove cooling bath and let warm to RT. After 15 min, quench the reaction with water then extract with EA. Wash the organics with water followed by aqueous saturated sodium chloride. Dry the organics over anhydrous magnesium sulfate. Filter and concentrate in vacuo to give the title compound (0.4 g, 93%). LCMS (4 min)=425.0, 427.0, M+1.

Preparation 9

4-((6-Chloro-3-(4-chloro-2-fluorobenzyl)-2-methylimidazo[1,2-b]pyridazin-8-yl)methyl)morpholine Combine (4-chloro-2-fluorophenyl)(6-chloro-2-methyl-8-(morpholinomethyl)imidazo[1,2-b]pyridazin-3-yl)methanol (0.4 g, 0.94 mmol), 1,2-dichloroethane (25 mL), triethylsilane (0.45 mL, 3 equiv.), and trifluoroacetic acid (0.57 mL, 8 equiv.) in a round bottom flask and place under nitrogen. Heat at 70° C. overnight. Concentrate reaction in vacuo. Load onto a Varian MegaElut® 10 gram SCX ion exchange cartridge (prewashed with methanol). Elute with methanol to remove non-basic impurities. Elute with 2 M ammonia in methanol. Concentrate in vacuo to give the title compound (0.36 g, 94%). LCMS (4 min)=409.0, 411.0, M+1.

Preparation 10

3-(4-Chloro-2-fluorobenzyl)-N-(1-(4-methoxybenzyl)-5-methyl-1H-pyrazol-3-yl)-2-methyl-8-(morpholinomethyl)imidazo[1,2-b]pyridazin-6-amine Combine 4-((6-chloro-3-(4-chloro-2-fluorobenzyl)-2-methylimidazo[1,2-b]pyridazin-8-yl)methyl)morpholin (0.36 g, 0.88 mmol), 1-(4-methoxybenzyl)-5-methyl-1H-pyrazol-3-amine (0.248 g, 1.3 equiv.), potassium carbonate (0.30 g, 2.5 equiv.), 4,5-bis(diphenylphosphino)-9,9-dimethylxanthene (0.076 g, 0.15 equiv.), water (2 mL), and 1,4-dioxane (20 mL) in a round bottom flask. Degas thoroughly with nitrogen then add bis(dibenzylideneacetone)palladium (0.10 g, 0.2 equiv.). Attach a reflux condenser and place under nitrogen. Heat the reaction at reflux overnight. Pass reaction through a Celite plug. Wash the plug with EA. Transfer to a separatory funnel and wash with water. Wash the organic layer with aqueous sodium chloride, and dry over anhydrous magnesium sulfate. Filter and concentrate in vacuo. Purify on silica gel (EA→10% methanol:EA) to give the title compound (0.447 g, 86%) as a pale yellow solid. LCMS (4 min)=590.2, 591.2, M+1.

Example 1

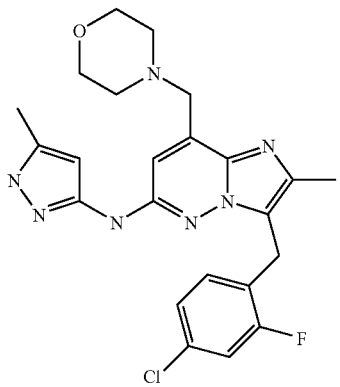

3-(4-Chloro-2-fluorobenzyl)-2-methyl-N-(5-methyl-1H-pyrazol-3-yl)-8-(morpholinomethyl)imidazo[1,2-b]pyridazin-6-amine Combine 3-(4-chloro-2-fluorobenzyl)-N-(1-(4-methoxybenzyl)-5-methyl-1H-pyrazol-3-yl)-2-methyl-8-(morpholinomethyl)imidazo[1,2-b]pyridazin-6-amine (0.447 g, 0.76 mmol) and trifluoroacetic acid (10 mL) in a 20 mL microwave reactor tube. Seal with a crimp cap then heat in a microwave reactor at 120° C. for 20 min. Partition between EA and water that is made basic with excess NaOH aqueous. Wash the organic phase three times with NaOH aqueous followed by aqueous saturated sodium chloride. Dry over anhydrous magnesium sulfate. Filter and concentrate in vacuo. Purify on silica gel (EA→10% methanol:EA) to give the title compound (0.246 g, 0.52 mmol) as a pale yellow solid. LCMS (8 min)=470.0, M+1.

Example 2

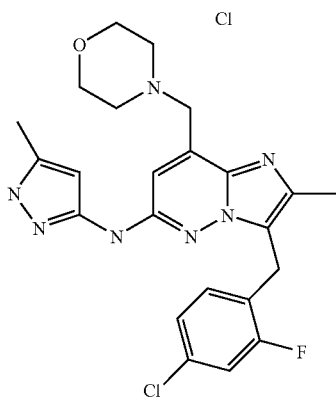

3-(4-Chloro-2-fluorobenzyl)-2-methyl-N-(5-methyl-1H-pyrazol-3-yl)-8-(morpholinomethyl)imidazo[1,2-b]pyridazin-6-amine hydrochloride Combine 3-(4-chloro-2-fluorobenzyl)-2-methyl-N-(5-methyl-1H-pyrazol-3-yl)-8-(morpholinomethyl)imidazo[1,2-b]pyridazin-6-amine (0.1 g, 0.21 mmol) and 1,4-dioxane (10 mL) in a pear flask and place under nitrogen. Add hydrogen chloride (4 M in 1,4-dioxane, 0.053 mL, 1.0 equiv.) and let stir at RT under nitrogen for 1.5 h. Concentrate in vacuo then evaporate under vacuum from absolute ethanol two times. Dry overnight in a vacuum oven (60° C.) to give the title compound (0.11 g, 102%). LCMS (8 min)=470.0, M+1.

SCHEME 2

Preparation 11

(E)-N'-(6-chloropyridazin-3-yl)-N,N-dimethylacetimidamide

Combine 6-chloropyridazin-3-amine (1.500 kg, 11.58 mol); 1,1-dimethoxy-N,N-dimethylethanamine (2.313 kg, 17.37 mol) and cyclopentyl methyl ether (8.25 L) then heat to 98° C. while distilling off the resulting methanol byproduct. After 4 h, the reaction mixture is cooled to ambient temperature and heptanes (11.2 L) is added to the reaction solution for crystallizing the product. The title compound is collected by filtration and is dried. (1.494 kg, 64.95%; mp=73° C.)

Preparation 12

2-chloro-1-(4-chloro-2-fluorophenyl)ethanone

Stir a mixture of heptanes (1.5 L), methanol (0.4 L), and 1-(4-chloro-2-fluorophenyl)ethanone (1 kg, 5.81 mol) with cooling to <5° C. Add sulfuryl chloride (0.608 L, 1.02 kg, 7.55 mol) as a heptanes (1.5 L) solution drop-wise to the mixture keeping the reaction temperature <15° C. during the addition. After 2 h quench the reaction at ambient temperature to a pH of 6 with sodium hydroxide (5N, 2.0 L). Extract the reaction mixture with methylene chloride (2 L) and concentrate the extract to form a white solid. Filter and dry the solid.

Preparation 13

(4-chloro-2-fluorophenyl)(6-chloro-2-methylimidazo[1,2-b]pyridazin-3-yl)methanone Combine 2-chloro-1-(4-chloro-2-fluorophenyl)ethanone (1.5 kg, 5.44 mol), and (E)-N'-(6-chloropyridazin-3-yl)-N,N-dimethylacetimidamide (1.19 kg, 5.72 mol) in DMF (10.14 L) and heat at 120° C. for 5 h. After cooling, add water (30 L) and stir to crystallize the product. Collect the product by filtration and rinse the cake with water (2×12 L) and heptanes (2×10 L) then dry under vacuum to obtain title compound. (1.490 kg, 84.44%; mp=160° C., M+=324).

Preparation 14

(4-chloro-2-fluorophenyl)(6-chloro-2-methyl-8-(morpholinomethyl)imidazo[1,2-b]pyridazin-3-yl)methanone Add ethanol (12 L), (4-chloro-2-fluorophenyl)(6-chloro-2-methylimidazo[1,2-b]pyridazin-3-yl)methanone (897.70 g, 2.77 mol) and bis(2,4-pentanedionato)oxovanadium (IV) (146.81 g, 553.67 mmol) to a reaction vessel with a nitrogen atmosphere. Add an ethanol (6 L) solution of 4-methylmorpholine 4-oxide (3.89 kg, 33.21 mol) drop-wise over 150 min keeping the reaction temperature at 23-33° C.; then heat the reaction at 40° C. for 48 h. Cool the reaction and concentrate by removal of solvent (13 L). Filter the resulting mixture, rinse the filter cake with hexane (1 L) and then dry. (728 g, 66.25%; mp 145-147° C.; M+=423).

Preparation 15

4-((6-chloro-3-(4-chloro-2-fluorobenzyl)-2-methylimidazo[1,2-b]pyridazin-8-yl)methyl)morpholine hydrochloride At 26° C., combine triethylsilane (110 g, 946 mmol) and (4-chloro-2-fluorophenyl)(6-chloro-2-methyl-8-(morpholinomethyl)imidazo[1,2-b]pyridazin-3-yl)methanone (50.1 g, 117.06 mmol) to form a solution. Add trifluoro acetic acid (150 mL, 1.98 mol) to the reaction mixture then heat at 78° C. for 24 h. Cool the reaction to ambient temperature and separate the mixture to remove the top layer. Dissolve the bottom layer with ethyl acetate (1 L) and adjust the pH to 11 with sodium hydroxide (4 N, 500 mL). Separate the organic layer and add HCl (4 M in ethyl ether) to the organic layer to form the HCl salt. Filter and dry the HCl salt. (100 g (96%); mp=237-238° C.; M+=409).

Preparation 16

3-(4-Chloro-2-fluorobenzyl)-2-methyl-N-(5-methyl-1H-pyrazol-3-yl)-8-(morpholinomethyl)imidazo[1,2-b]pyridazin-6-amine hydrochloride and freebase Prepare active catalyst by combining palladium chloride (160 mg, 0.90 mmol) and 4,5-bis(diphenylphosphino)-9,9-dimethylxanthene (1.10 g, 1.84 mmol) in DMF (25 mL) and warming to form a solution. Add the preformed catalyst to a solution of 3-methyl-1H-pyrazol-5-amine (3.0 g, 29.65 mmol), 4-((6-chloro-3-(4-chloro-2-fluorobenzyl)-2-methylimidazo[1,2-b]pyridazin-8-yl)methyl)morpholine hydrochloride (9.0 g, 20.19 mmol), potassium bicarbonate (6.0 g, 59.93 mmol) in DMF (65 mL) and heat to 150° C. for 1 h. Cool the reaction to 60° C. and add mercaptopropyl functionalized silica (500 mg) and stir for 1 h then filter to remove the silica. Cool to ambient temperature, add 2-methyltetrahydrofuran (125 mL) and extract with water to remove DMF. Add HCl to the organic solution to form the 3-(4-chloro-2-fluorobenzyl)-2-methyl-N-(5-methyl-1H-pyrazol-3-yl)-8-(morpholinomethyl)imidazo[1,2-b]pyridazin-6-amine hydrochloride salt. Add the HCl salt (1.1 g) to sodium hydroxide (10 mL, 1N) in n-butanol (10 mL) and stir. Filter the resulting mixture to obtain 0.22 g of the free base, imidazo[1,2-b]pyridazin-6-amine, 3-[(4-chloro-2-fluorophenyl)methyl]-2-methyl-N-(5-methyl-1H-pyrazol-3-yl)-8-(4-morpholinylmethyl), (22% yield, M+1.=470).

Example 3

Formulation of 3-(4-Chloro-2-fluorobenzyl)-2-methyl-N-(5-methyl-1H-pyrazol-3-yl)-8-(morpholinomethyl)imidazo[1,2-b]pyridazin-6-amine Optionally pass 3-(4-chloro-2-fluorobenzyl)-2-methyl-N-(5-methyl-1H-pyrazol-3-yl)-8-(morpholinomethyl)imidazo[1,2-b]pyridazin-6-amine and excipients through an appropriate screen. Combine and blend 3-(4-chloro-2-fluorobenzyl)-2-methyl-N-(5-methyl-1H-pyrazol-3-yl)-8-(morpholinomethyl)imidazo[1,2-b]pyridazin-6-amine, Pregelatinized Starch, and Pregelatinized Starch with 5% Dimethicone using an appropriate tumble bin (with or without intensifier bar) or other suitable mixing equipment. Alternately, add dimethicone during blending via a liquid addition system. Fill the blended powder into capsules using suitable encapsulation equipment. Monitor weight uniformity and appropriate in-process parameters during the filling process. Optionally dedust the final capsules or polish by either manual or automated processes.

JAK2 EPO-TF1/pSTAT5 Cell-Based Assay

Cellomics ArrayScan® HCS

JAK2 EPO-TF1/pSTAT5 cell-based assay mimics the constitutive activation of JAK2-STAT5 in erythroid progenitor cells, which drives the overproduction of red blood cells, a marker of polycythemia vera (PV).

TF-1 (human erythroid leukemia) cells are maintained in RPMI 1640 (RPMI-1640 was developed by Moore et. al. at Roswell Park Memorial Institute. The formulation is based on the RPMI-1630 series of media utilizing a bicarbonate buffering system and alterations in the amounts of amino acids and vitamins.) with 10% fetal bovine serum (FBS), 0.075% sodium bicarbonate, 1 mM sodium pyruvate, 1× antibiotic/antimycotic (Invitrogen, Carlsbad, Calif.) and 0.45% glucose. The medium is supplemented with GM-CSF (granulocyte-macrophage colony-stimulating factor) at a final concentration of 2 ng/mL. Cells are kept at 37° C. with 5% $CO_2$. Cells are starved in serum free medium to remove endogenous growth factors. TF-1 cells are counted and cells are collected to seed $2 \times 10^7$ cells per 96-well plate at a density of $2 \times 10^5$ cells per well. The cells are rinsed twice with unsupplemented RPMI 1640 (RPMI 1640 with 0.075% sodium bicarbonate, 1 mM sodium pyruvate, 1× antibiotic/antimycotic, and 0.45% glucose) before suspending cells at a final concentration of $5 \times 10^5$ cells/mL in RPMI with 0.6% FBS. The diluted cells are added back to tissue culture flasks and incubated overnight at 37° C. Test compounds are prepared in 100% DMSO at 10 mM concentration. Compounds are serially diluted 1:3 with 100% DMSO in a 10 point-200× concentration-response range (4 mM-200 nM). In a separate 96 deep well plate 2.5 μL of 200× compound solution is added to 125 μL of complete RPMI 1640 media with 10% FBS for a 4× concentration compound plate.

To perform the assay, serum-starved cells are collected and washed once with unsupplemented RPMI 1640 medium. Cells are suspended in 10% FBS complete RPMI medium for a final concentration of $8 \times 10^5$ cells/mL. An aliquot of 250 μL of diluted cells ($2 \times 10^5$ cells) are added to each well in the 4× concentration compound plate. Cells are mixed by vortexing and the plate is incubated in a 37° C. water bath for 10 min. A fresh 4× working solution of Erythropoietin (EPO) at 6.4 Units/mL is prepared by using pre-warmed 10% FBS complete RPMI 1640 medium. After the cells are treated with compound for 10 min, 125 μL of EPO medium is added into each well and the plate is vortexed. Cells are incubated in a 37° C. water bath for 20 min and mixed every 5 min during the incubation time. Final 10 point concentration-response range is 20 μM-1 nM at a final concentration of DMSO at 0.5% and EPO at 1.6 U/mL. After cell treatment, 500 μL of 1% formaldehyde solution (made freshly with phosphate-buffered saline (PBS) and kept warm at 37° C.) is added to each well. Plates are sealed and inverted 8-10 times to mix. Plates are placed in a 37° C. water bath for 10 min. After incubation, cell plates are spun at 1200 rpm for 5 min at room temperature (RT). The supernatant is aspirated, leaving 100 μL of cells ($2 \times 10^5$ cells). The cells are vortexed and washed twice with 800 μL of PBS by repeating the spin steps and leaving 100 μL containing $\sim 2 \times 10^5$ cells after the final wash. An aliquot of 800 μL of cold 90% methanol is added to the cells and placed at −20° C. overnight. Plates are spun and methanol is removed. Cells are washed with FACS buffer (PBS with 5% FBS and 0.02% sodium azide). An aliquot of 200 μL of 1 to 10 dilution of Mouse anti-pSTAT5 (pY694) Alexa Fluor 647® in fluorescence activated cell sorting (FACS) buffer is added to the cells. Cells are mixed well and incubated at RT in the dark for 2 h. Cells are washed once with PBS and 100 μL of cells are left. A working solution of 2 μg/mL Hoechst (Acros Organics, Morris Plains, N.J.) is prepared with PBS. An aliquot of 200 μL is added to each well and cells are incubated at RT in the dark for 10 min. Cells are washed with PBS, and 50 μL of Cytofix (BD Biosciences, San Jose, Calif.) is added to the cells. The cells are transferred to 96 well black tissue culture plates and sealed. The plates are spun down. Mean fluorescent intensity data are collected and analyzed using Cellomics Arrayscan® VTi. Compound treatment is compared to the vehicle to determine percent inhibition data. The minimum significant ratio (MSR) between two test compounds with different $IC_{50}$s is determined to be 2.2. The relative $IC_{50}$ is calculated using a 4 parameter logistic curve fitting analysis with ActivityBase 4.0. For 3-(4-chloro-2-fluorobenzyl)-2-methyl-N-(5-methyl-1H-pyrazol-3-yl)-8-(morpholinomethyl)imidazo[1,2-b]pyridazin-6-amine, the $IC_{50}$=0.033 μM, n=4. The results of this assay demonstrate that 3-(4-chloro-fluorobenzyl)-2-methyl-N-(5-methyl-1H-pyrazol-3-yl)-8-(morpholinomethyl)imidazo[1,2-b]pyridazin-6-amine is a potent JAK2 inhibitor.

JAK3 IL-2-NK-92/pSTAT5 Cell-Based Assay

Cellomics ArrayScan® HCS

IL-2 activates the JAK3 pathway in natural killer (NK) cells to drive the NK and CD8 lymphocyte proliferation. Therefore, IL-2 stimulated NK92/pSTAT5 cell-based assay enables the evaluation of the JAK3 cellular activity of JAK2 compounds in vitro.

NK-92 (natural killer) cells (ATCC, Manassas, Va.) are maintained in minimum essential medium (MEM) Alpha with 15% fetal bovine serum, 15% Horse Serum and 1× antibiotic/antimycotic (Invitrogen, Carlsbad, Calif.). The medium is supplemented with IL-2 (R&D systems, Minneapolis, Minn.) for a final concentration of 4 ng/mL. Cells are kept at 37° C. with 5% $CO_2$. Cells are starved in serum free medium to remove endogenous growth factors. NK-92 cells are counted and collected to seed $2 \times 10^7$ cells per 96-well plate at a density of $2 \times 10^5$ cells per well. The cells are rinsed twice with unsupplemented MEM Alpha (MEM Alpha) before suspending cells at a final concentration of $8 \times 10^5$ cells/mL in MEM Alpha with 0.6% serum (0.3% FBS, 0.3% horse serum). The diluted cells are added back to tissue culture flasks and incubated overnight at 37° C. Test compounds are prepared in 100% DMSO at 10 mM concentration. Compounds are serially diluted 1:3 with 100% DMSO in a 10 point-200× concentration-response range (4 mM-200 nM). In a separate 96 deep well plate 2.5 μL of 200× compound solution is added to 125 μL of 10% FBS complete RPMI 1640 medium for a 4× concentration compound plate.

To perform the assay, serum-starved cells are collected and washed once with unsupplemented RPMI 1640 medium. Cells are suspended in 10% FBS complete RPMI 1640 medium for a final concentration of $8 \times 10^5$ cells/mL. An aliquot of 250 μL of diluted cells ($2 \times 10^5$ cells) is added to each well in the 4× concentration compound plate. Cells are mixed by vortexing and the plate is incubated in a 37° C. water bath for 10 min. A fresh 4× working solution of IL-2 at 2 ng/mL is prepared using pre-warmed 10% FBS complete RPMI medium. After the cells are treated with compound for 10 min, 125 μL of IL-2 medium is added into each well. Cells are mixed by vortexing. Cells are incubated in a 37° C. water bath for 20 min and mixed every 5 min during the incubation time. Final 10 point concentration-response range is 20 μM-1 nM at a final concentration of DMSO at 0.5% and IL-2 at 0.5 ng/mL. After cell treatment, 500 μL of 1% formaldehyde solution (made freshly with phosphate-buffered saline (PBS) and kept warm at 37° C.) is added to each well. Plates are sealed and inverted 8-10 times to mix. Plates are placed in a 37° C. water bath for 10 min. After incubation, cell plates are spun at 1200 rpm for 5 min at RT. The supernatant is aspirated, leaving 100 μL of cells ($2 \times 10^5$ cells). The cells are vortexed and washed twice with 800 μL of PBS by repeating the spin steps and leaving 100 μL containing ~$2 \times 10^5$ cells after the final wash. An aliquot of 800 μL of cold 90% methanol is added to the cells and placed at −20° C. overnight. Plates are spun and methanol is removed. Cells are washed with FACS buffer (PBS with 5% FBS and 0.02% sodium azide). An aliquot of 200 μL of 1 to 10 dilution of Mouse anti-pSTAT5 (pY694) Alexa Fluor 647° in fluorescence activated cell sorting (FACS) buffer is added to the cells. Cells are mixed well and incubated at RT in the dark for 2 h. Cells are washed once with PBS and 100 μL of cells are left. A working solution of 2 μg/mL Hoechst (Acros Organics, Morris Plains, N.J.) is prepared with PBS. An aliquot of 200 μL is added to each well and cells are incubated at RT in the dark for 10 min. Cells are washed with PBS, and 50 μL of Cytofix® (BD Biosciences, San Jose, Calif.) is added to the cells. The cells are transferred to 96 well black tissue culture plates and sealed. The plates are spun down. Mean fluorescent intensity data are collected and analyzed using Cellomics Arrayscan® VTi. Compound treatment is compared to the vehicle to determine percent inhibition data. The MSR is determined to be 2.06. The relative $IC_{50}$ is calculated using a 4 parameter logistic curve fitting analysis with ActivityBase 4.0. For 3-(4-chloro-2-fluorobenzyl)-2-methyl-N-(5-methyl-1H-pyrazol-3-yl)-8-(morpholinomethyl)imidazo[1,2-b]pyridazin-6-amine, the $IC_{50}$=0.94 μM, n=4. The results of the JAK3 IL2-NK92-pSTAT5 cell-based assay demonstrate that 3-(4-chloro-2-fluorobenzyl)-2-methyl-N-(5-methyl-1H-pyrazol-3-yl)-8-(morpholinomethyl) imidazo-[1,2-b]pyridazin-6-amine is a less potent inhibitor of JAK3 (when compared to the results of the JAK2 EPO-TF1/pSTAT5 cell based assay with an $IC_{50}$=0.033 uM). From these results, the ratio of JAK3/JAK2, the $IC_{50}$ was determined to be 28.5 fold, which demonstrates 3-(4-chloro-2-fluorobenzyl)-2-methyl-N-(5-methyl-1H-pyrazol-3-yl)-8-(morpholinomethyl)imidazo[1,2-b]pyridazin-6-amine is a selective JAK2 inhibitor over JAK3.

Ba/F3JAK2V617F Cell-Based Assay

Cellomics ArrayScan® HCS

JAK2 target inhibition has been evaluated in Ba/F3 expressing JAK2 V617F by Western blot as reported in Wernig et al. (Wernig G, et al. *Efficacy of TG101348, a selective JAK2 inhibitor, in treatment of a murine model of JAK2V617F-induced polycythemia vera*, Cancer Cell, April; 13(4):311-20). A medium throughput Cellomics assay was established to evaluate the JAK2 target inhibition in Ba/F3 cells expressing JAK2V617F. This assay enables the discovery of an effective therapeutic agent to treat disorders associated with JAK2V617F mutation.

Ba/F3 (murine pro-B) cells expressing JAK2V617F maintained in RPMI 1640 with 10% FBS, 0.07% sodium bicarbonate, 1 mM sodium pyruvate, 1× antibiotic/antimycotic (Invitrogen, Carlsbad, Calif.) and 0.45% glucose (Sigma, St Louis, Mo.). Cells are kept at 37° C. with 5% $CO_2$. The test compound is prepared in 100% DMSO at 10 mM concentration. The compound is serially diluted 1:3 with 100% DMSO in a 10 point 200× concentration-response range (4 mM-200 nM.). In a separate 96 deep well plate 2.5 µL of 200× compound solution is added to 125 µL of complete RPMI 1640 media with 10% FBS for a 4× concentration compound plate.

To perform the assay, cells are collected and washed twice with unsupplemented RPMI 1640. Cells are then suspended in 10% FBS completed RPMI medium for a final concentration of $4\times10^5$/mL. Next, 500 µL of cells ($2\times10^5$ cells) are transferred into 96 deep well plates. Finally, 2.5 µL (1:200 dilution) of compound stock solution are added to the cells and are incubated with cells in a 37° C. water bath for 60 min.

After cell treatment, 500 µL of 1% formaldehyde solution (made freshly with phosphate-buffered saline (PBS) and kept warm at 37° C.) is added to each well. Plates are sealed and inverted 8-10 times to mix. Plates are placed in a 37° C. water bath for 10 min. After incubation, cell plates are spun at 1200 rpm for 5 min at RT. The supernatant is aspirated, leaving 100 µL of cells ($2\times10^5$ cells). The cells are vortexed and washed twice with 800 µL of PBS by repeating the spin steps and leaving 100 µL containing ~$2\times10^5$ cells after the final wash. An aliquot of 800 µL of cold 90% methanol is added to the cells and placed at -20° C. overnight. Plates are spun and methanol is removed. Cells are washed with FACS buffer (PBS with 5% FBS and 0.0% sodium azide). An aliquot of 200 µL of 1 to 10 dilution of Mouse anti-pSTAT5 (pY694) Alexa Fluor 647® in fluorescence activated cell sorting (FACS) buffer is added to the cells. Cells are mixed well and incubated at RT in the dark for 2 h. Cells are washed once with PBS and 100 µL of cells are left. A working solution of 2 µg/mL Hoechst (Acros Organics, Morris Plains, N.J.) is prepared with PBS. An aliquot of 200 µL is added to each well and cells are incubated at RT in the dark for 10 min. Cells are washed with PBS, and 50 µL of Cytofix® (BD Biosciences, San Jose, Calif.) is added to the cells. The cells are transferred to 96 well black tissue culture plates and sealed. The plates are spun down. Mean fluorescent intensity data are collected and analyzed using Cellomics Arrayscan® VTi. Compound treatment is compared to the vehicle to determine percent inhibition data. The relative $IC_{50}$ is calculated using a 4 parameter logistic curve fitting analysis with ActivityBase 4.0. For 3-(4-chloro-2-fluorobenzyl)-2-methyl-N-(5-methyl-1H-pyrazol-3-yl)-8-(morpholinomethyl)imidazo[1,2-b]pyridazin-6-amine, the $IC_{50}$=0.03 µM. The results of this assay demonstrate that 3-(4-chloro-2-fluorobenzyl)-2-methyl-N-(5-methyl-1H-pyrazol-3-yl)-8-(morpholinomethyl)imidazo[1,2-b]pyridazin-6-amine effectively inhibits the JAK2V617F target in Ba/F3 cells expressing JAK2V617F gene.

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19th ed., Mack Publishing Co., 1995).

The compounds of the present invention are generally effective over a wide dosage range. For example, dosages per day normally fall within the range of about 1 mg to about 1000 mg total daily dose, preferably 500 mg to 1000 mg total daily dose, more preferably 600 mg to 1000 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound which is 3-(4-chloro-2-fluorobenzyl)-2-methyl-N-(5-methyl-1H-pyrazol-3-yl)-8-(morpholinomethyl)imidazo[1,2-b]pyridazin-6-amine, or a pharmaceutically acceptable salt thereof.

2. The compound according to claim 1 which is 3-(4-chloro-2-fluorobenzyl)-2-methyl-N-(5-methyl-1H-pyrazol-3-yl)-8-(morpholinomethyl)imidazo[1,2-b]pyridazin-6-amine.

3. The compound according to claim 1 which is 3-(4-chloro-2-fluorobenzyl)-2-methyl-N-(5-methyl-1H-pyrazol-3-yl)-8-(morpholinomethyl)imidazo[1,2-b]pyridazin-6-amine hydrochloride.

4. A pharmaceutical composition comprising a compound according to claim 1, or a pharmaceutically acceptable salt thereof, and a pharmaceutically acceptable carrier, diluent or excipient.

5. A pharmaceutical composition comprising a compound according to claim 3, and a pharmaceutically acceptable carrier, diluent or excipient.

6. The compound according to claim 3 for use in the treatment of glioblastoma, breast cancer, multiple myeloma, prostate cancer, atypical chronic myeloid leukemia, primary and secondary acute myeloid leukemia, T-lineage and B-lineage acute lymphoblastic leukemia, myelodysplasia syndrome, and chronic myeloproliferative disorders selected from the group consisting of polycythemia vera, essential thrombocytosis, and myelosclerosis with myeloid metaplasia.

7. The compound for use according to claim 6, or a pharmaceutically acceptable salt thereof, in the treatment of chronic myeloproliferative disorders selected from the group consisting of polycythemia vera, essential thrombocytosis, and myelosclerosis with myeloid metaplasia.

8. The compound according to claim 1 for use in the treatment of glioblastoma, breast cancer, multiple myeloma, prostate cancer, atypical chronic myeloid leukemia, primary and secondary acute myeloid leukemia, T-lineage and B-lineage acute lymphoblastic leukemia, myelodysplasia syndrome, and chronic myeloproliferative disorders selected from the group consisting of polycythemia vera, essential thrombocytosis, and myelosclerosis with myeloid metaplasia.

9. The compound for use according to claim 8, or a pharmaceutically acceptable salt thereof, in the treatment of chronic myeloproliferative disorders selected from the group consisting of polycythemia vera, essential thrombocytosis, and myelosclerosis with myeloid metaplasia.

* * * * *